(12) United States Patent
Starek et al.

(10) Patent No.: US 7,401,526 B2
(45) Date of Patent: * Jul. 22, 2008

(54) FORCE MEASURING TRANSDUCER

(75) Inventors: Bruno Starek, Kobersdorf (AT); Franz Vekoerrer, Rotkreuz (CH); Helmut Purner, Koestendorf (AT)

(73) Assignee: Occluscan AG, Rotkreuz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/580,681

(22) Filed: Oct. 13, 2006

(65) Prior Publication Data

US 2007/0039394 A1    Feb. 22, 2007

Related U.S. Application Data

(63) Continuation of application No. 10/944,451, filed on Sep. 17, 2004, now Pat. No. 7,121,148.

(30) Foreign Application Priority Data

Sep. 18, 2003  (EP)  .................................. 03021248

(51) Int. Cl.
     *G01B 7/16* (2006.01)
(52) U.S. Cl. ........................................ 73/778
(58) Field of Classification Search ............ 73/778
     See application file for complete search history.

(56) References Cited

U.S. PATENT DOCUMENTS

| 3,617,878 | A |   | 11/1971 | Senour |
| 4,006,628 | A |   | 2/1977  | St. Jacques |
| 4,345,237 | A | * | 8/1982  | Lerche et al. ............... 340/946 |
| 4,592,727 | A |   | 6/1986  | Bloomfield |
| 7,093,498 | B2| * | 8/2006  | Herbert et al. ................ 73/778 |
| 7,121,148 | B2| * | 10/2006 | Starek et al. .................. 73/778 |

FOREIGN PATENT DOCUMENTS

| DE | 37 35 657 A1 | 5/1988 |
| DE | 44 20 691 C1 | 1/1996 |
| GB | 1 585 549    | 3/1981 |
| JP |    5-31130   | 2/1993 |

* cited by examiner

*Primary Examiner*—Max Noori
(74) *Attorney, Agent, or Firm*—Flynn, Thiel, Boutell & Tanis, P.C.

(57) ABSTRACT

The invention relates to a force measuring transducer with an oscillator (1) with an inductor (2) formed by a primary winding and a gauge (11) with a secondary winding (30) which is connected electroconductively to the gauge (11) and which is disposed in transformer coupling with the inductor (2) of the oscillator (1). Action of a force on the gauge (11) changes the impedance of the gauge (11) and the load of the inductively coupled secondary winding (30). An evaluation circuit (14) is used to determine the resulting frequency change of the oscillator (1) which is proportional to the force acting on the gauge (11).

29 Claims, 9 Drawing Sheets

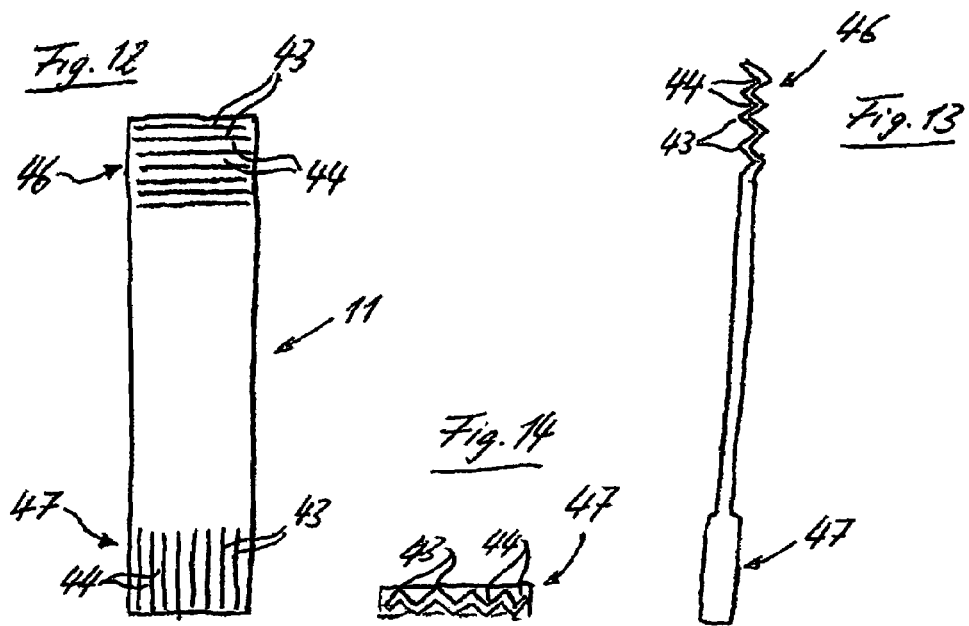
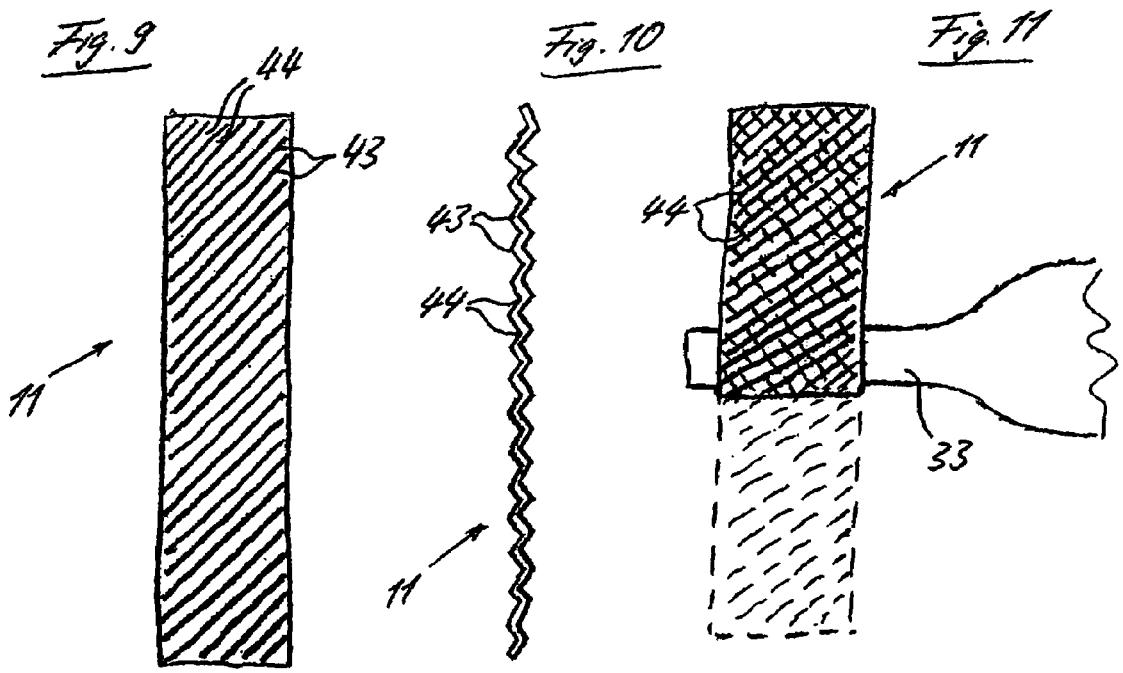

FORCE MEASURING TRANSDUCER

This application is a continuation of U.S. patent application Ser. No. 10/944,451 filed Sep. 17, 2004 now U.S. Pat. No. 7,121,148, the disclosure of which is hereby incorporated by reference.

This invention relates to a measuring transducer for determining physical or mechanical quantities. Force as intended by the invention includes according to the invention all quantities definable by force, such as pressure, acceleration, torsion, etc. In connection with the inventive use of a gauge with pyroelectric properties, temperature can also be determined.

Numerous measuring transducers are known for determining physical or mechanical quantities. Depending on the measuring principle, the forces acting on such measuring transducers are detected via an influencing of inductance, capacitance or resistance, whereby the particular measurand based on the measuring principle can be accompanied by further parasitical influences, which will not be dealt with below.

Known gauges are usually of very complicated and thus expensive structure both electronically and mechanically, and are accordingly very susceptible. The gauge provided is mostly a mechanically elaborate and therefore expensive force transmission element, which is occasionally unsuitable for thin sensors.

DE 37 35 657 A1 discloses a device for measuring the extension of solid bodies, in particular internal extension events, whereby an inductor is incorporated into the solid body during the production process and the change of inductance determines the measure of extension. The structure of this measuring device is very complex and elaborate and cannot be used for small or thin sensors. A further disadvantage is the inflexible change of place of the sensor. Further, there is a galvanic coupling, so that interference can occur.

DE 44 20 691 C1 discloses a load cell which has an elastically deformable force sensor for sensing the weight and an inductor disposed adjacent thereto, whereby the eddy current effect is used due to the sensor arrangement. The abovementioned disadvantages are present here, too.

The present invention has the great advantage that in combination with inductive, capacitive and/or ohmic gauges, measurements can be carried out in the low-impedance range, for example 1 ohm. Thus, interference is avoided better in comparison to the measurement ranges of known transducers and no costly structural designs are necessary for complying with safety regulations. Further, the invention is advantageous in that it is suitable in its special embodiments for very thin sensors, for example a thickness of under 20 microns in the gauging area, and the gauge can inherently be positioned without any elaborate measures.

Due to the galvanic isolation of the gauge from the oscillator circuit, interference on the oscillator can moreover be avoided.

In particular the invention is very well suited for the application of gauges under rough conditions, such as dirt, moisture, etc.

According to the invention, the action of a physical or mechanical quantity on the gauge causes a change of impedance therein which in turn changes the load in the secondary winding which is connected electrically (conductively) to the gauge and which is coupled in transformer arrangement to the inductor of the oscillator. This change of impedance or load causes the frequency of the oscillator to be changed proportionally to the physically acting quantity (e.g. force) and this frequency change is evaluated and detected as an electrical measurand.

In numerous applications, transducers with piezoelectric sensors are used for measuring physical and mechanical quantities such as force, pressure, torsion, acceleration, temperature, etc.

However, piezoelectric sensors have the known disadvantage of requiring for measurement value logging an electronic voltage amplifier with a very high-value input resistance with high-grade insulation or a so-called charge amplifier. Such electrometer or charge amplifiers are firstly very complicated in structure and therefore expensive to produce, and such amplifiers secondly offer further sources of possible interference.

A further known disadvantage of piezoelectric sensors is that they can inherently detect no static loads. Measuring transducers for carrying out only "quasi-static" measurements with piezoelectric sensors are known from EP 04 59 069 A1, but such transducers again require an expensive and elaborate charge amplifier with corresponding insulation resistances.

The advantage of the invention is the use of an inventive force measuring transducer with a piezoelectric or piezoresistive gauge whose electrodes are electrically connected to the secondary winding of the inductor of the oscillator. The action of force on the piezoelectric or piezoresistive gauge changes the capacitance or resistance and thus the impedance of the gauge. This impedance change causes a change of load in the secondary winding and this leads via the transformer coupling to a change of frequency of the oscillator. Due to this inventive measuring principle, no charge or electrometer amplifier is required and static measurements are also possible.

This measurement setup offers the abovementioned advantages for all piezoelectric measuring transducers, such as quartz, piezoelectric ceramic, piezoelectric polymers, such as PVDF and copolymers thereof, polymers with piezoelectric particles or piezoelectric fibers, piezoelectric foams, ferroelectrets, etc., but also for piezoresistive measuring transducers, such as silicon.

Upon use of a piezoelectric gauge with pyroelectric properties, temperature changes cause a change of polarization of the piezoelectric material of the gauge, which can in turn be detected by the electrodes and measured as a frequency change in the oscillator as described above. Thus, the inventive force measuring transducer also permits the determination of temperatures. An inventive force measuring transducer can thus be used to measure e.g. vehicle tire pressure and vehicle tire temperature at the same time in a very simple and economical way.

The inventive measuring force transducer with a gauge with piezoelectric properties can of course also be used in combination with a seismic mass for determining acceleration.

Preferably, upon use of a gauge with piezoelectric, piezoresistive or pyro-electric properties, the secondary winding electrically connected thereto is disposed in transformer coupling around a magnetically soft ring core, for example made of ferrite. Thus, scattering losses of the magnetic field are avoided for the most part and there is an "ideal" coupling.

For application fields requiring very thin or three-dimensional gauges, such as dental applications, the inventive gauge preferably used is a piezoelectric foil (PVDF and copolymers thereof) with a thickness under 80 microns, preferably under 30 microns, or a liquid PVDF copolymer lacquer, which can be cast or sprayed very thin.

The abovementioned advantages can also be obtained for gauges formed from piezoelectric foams or so-called ferroelectrets.

For determining the occlusion contact between two pressed together bodies, staining or discoloring foils are used in dentistry for example, whereby the contact between maxillary and mandibular teeth leads to discoloration of the foil but also to staining of the contact points on the teeth. Further, the foil can have a color layer with a dye enclosed in capsules. Depending on the pressure force acting on the color layer, a different number of capsules is broken open and thus a different amount of dye released. However, such foils do not permit exact determination of the strength of the pressure force, in particular the occlusion pressure between teeth.

For determining occlusion pressure, electrical pressure sensors are therefore also known. Thus, DE 31 17 284 A1, U.S. Pat. No. 4,521,186 and EP 0 379 524 B1 use sensors which consist of two layers each provided with track conductors and between which a resistance layer is provided. The action of pressure on the bite portion of the sensor changes the resistance between the track conductors of the two layers, and this change is detected as a measurand.

Known sensors are relatively complicated in structure and handling, so that they have not been able to gain wider acceptance than conventional occlusion contact foils with discoloration. Moreover, known sensors have a relatively thick bite portion, which detracts from the precision of occlusion measurement. Moreover, electrical contacting of the two layers with the track conductors must be effected for supplying the input and output signals. Since the bite portion must be changed in every patient for hygienic reasons, this involves additional effort.

Substantially the same disadvantages are found in occlusion pressure sensors based on the piezoelectric effect (e.g. U.S. Pat. No. 4,592,727). Additionally, known piezoelectric sensors have the disadvantage of being susceptible in adverse environmental conditions (such as water, dirt, oil, etc.) due to the required amplifier with a high-value input resistance. DE 197 05 569 C1 departs from electrical sensors in the bite area, instead proposing occlusion force transmission with pressurizing fluid.

The problem of the invention is also to provide a simply constructed apparatus for exactly determining the pressure between two pressed together bodies, in particular the dental contact pressure, which for example in the application field of dentistry can be handled like the conventional occlusion foil with discoloration, and in particular requires no electrical contacting in the bite area.

An inventive apparatus makes it possible in particular to determine the dental contact pressure occurring between teeth when the upper and lower jaws are closed. This dental contact pressure measurement also permits determination of the distance between the pressed together teeth.

According to the invention an oscillator with at least one inductor is provided for determining an acting physical or mechanical force. Instead of one oscillator, two or more oscillators can also be provided, for example a measuring and a reference oscillator. The difference of frequency of the two oscillators can be represented here audibly e.g. according to the so-called beat-frequency principle.

The oscillator for the inventive use has a certain natural frequency which can be for example in the range between 10 kHz and 1 GHz. The oscillator can be a self-oscillating oscillator or be activated by an oscillation generator.

Any known LC oscillator can fundamentally be used, such as a Meissner, Hartley or Colpitts oscillator; one can also use RL and quartz generators. However, it is preferable to use oscillators provided with inverters, in particular Schmitt trigger inverters, NAND and/or NOR gates. Such oscillators are interesting because they have a very simple and economical structure. It has proved especially suitable to use a circuit employing a frequency-fixing inductor as a transconductance between input and output in the inverter circuit.

The inductor is preferably formed of a primary winding with a magnetically soft core, preferably of a bar or ring core made of ferrite, but an air core coil is also fundamentally suitable for the inventive measuring principle. A ring core has the advantage that the magnetic scattering of the inductance is reduced over a bar core and thus the transformer coupling improved. This improves the frequency change in the oscillator.

The secondary winding of the inductor is connected electroconductively with the gauge according to the invention. The gauge has ohmic and/or capacitive and/or inductive properties. The action of force on the gauge changes the (transition) resistance and/or capacitance and/or permeability and thus the impedance of the gauge depending on the execution thereof. This impedance change influences/changes the load in the secondary winding disposed in transformer coupling with the inductor, thereby changing the frequency of the oscillator. This frequency change, which takes place proportionally to the acting force, is evaluated in the evaluation circuit.

The force can be determined according to the invention numerically by measurement units or e.g. also as a relative measurement not based on units. Determination of the force also makes it possible to determine the distance between the pressed together bodies or between the teeth in particular in the dental application for determining dental contact pressure or chewing pressure and occlusion.

An inventive execution is intended in particular for determining the contact pressure occurring between teeth, but it can be used in general for determining the pressure between two pressed together bodies.

A special formation of the gauging area of a gauge strip used (elevations/depressions with intersecting peaks) also permits the user to determine sliding of the teeth, i.e. additional dynamic lateral motion.

The gauge can be formed for example by an electroconductive foil or an electroconductive wire. Further, the gauge can be formed for example of a piezoelectric wafer in which the electrodes are electrically connected to the secondary winding and which is to be disposed around the inductance coil in transformer coupling. For the dental application the gauge is formed, in a preferred variant, integrally with the secondary winding as a simple foil and is wound as a gauge strip at least once around the inductor of the oscillator, which is preferably located in a thin, rod-shaped housing. Upon occlusion of the teeth the gauge strip gauging areas located therebetween touch, thereby changing the transition resistance, which leads to a frequency change of the oscillator via the transformer coupling.

The secondary winding and/or integrally formed gauge strip are wound at least once around the inductor of the oscillator. If they are wrapped around the inductor several times, the gauge effect is increased.

Quite generally, the invention permits the measurement range or sensitivity of measurement to be coordinated with the particular application field via the transformation ratio of primary winding and secondary winding.

The gauge can also be formed by a material with electroconductive properties which is provided with an electrically insulating layer at least in the pressure-absorbing area of the pressed together bodies. Said electrically insulating layer can be formed for example by an electrically insulating plastic or for example also by a metal oxide. Said electrically insulating layer can be destroyed in the area of the contact areas upon action of pressure of the pressed together bodies, so that this influences the transition resistance. This permits the inventive apparatus to be coordinated with the measurement ranges required in a great variety of application fields by the choice of thickness of the electrically insulating layer of the gauge.

In a preferred embodiment, the electroconductive gauge is formed of aluminum and has a natural alumina layer or an anodic coating in at least one gauging area.

However, the gauge need not fundamentally have an electrically insulating layer destructible by the action of pressure. It is instead possible to use a gauge made of electroconductive material whose transition resistance changes, for example in the range of 0.1 milliohms to 100 milliohms, when the two bodies or teeth are pressed together to cause a frequency shift of the oscillator.

When dental contact pressure is determined, the electroconductive foil can be formed for example as a gauge strip. Further, the gauge strip can be formed by a foil made of electroconductive material and be provided, for example on its inside, with an electrically insulating layer. The electroconductive material is in particular a metallic material, for example an aluminum or copper material, that is, aluminum or an aluminum alloy or copper or a copper alloy. Instead of a metal foil, however, an electroconductive plastic film can also be used for example. The electrically insulating layer of the gauge strip can be for example a metal oxide or for example also a piezoelectric layer. Obviously, if an electrically insulating layer is present it must be provided only in that area of the gauge strip that is located between the pressed together bodies or teeth. The gauge strip can also be provided with an electrically insulating layer on the outside.

The gauge can further be formed of an electroconductive material and an electrically insulating material with ferroelectric properties, for example an electrically insulating layer with ferroelectric properties. Piezoelectric materials are preferably used here. The high dielectric constant of these materials gives rise to an additional capacitive load in the gauge, which leads to a frequency change of the oscillator. The dielectric constant is influenced by a change of pressure between the pressed together bodies.

A further advantage of the inventive apparatus is that if a piezoelectric element is used as part of the gauge, no amplifier is required therefor since said element is coupled to the sensor electronics with low impedance as a capacitive load. This permits determination of the pressure between two pressed together bodies even under adverse environmental conditions, in particular in the moist surroundings of dentistry.

The gauge, in particular the foil or gauge strip, can also be formed of a ferromagnetic material, in particular a ferromagnetic material with magnetoelastic properties. Thus, amorphous alloys, so-called metallic glass, have proved suitable. Materials with magnetoelastic properties are characterized by the fact that their permeability changes upon mechanical load. The use of materials with ferromagnetic properties permits an improvement in the gauging effect through stronger influencing of inductance.

The gauge preferably formed as a gauge strip can consist of a plurality of layers which consist alternately of an electroconductive and an electrically insulating material. In such a gauge strip the layers of electroconductive material form a plurality of windings which can be activated in succession parallel to the sequence of the action of pressure of the pressed together bodies. Thus, the number or choice of layer materials permits different measurement and proportional ranges.

Further, it is provided that further functional layers are applied to the electroconductive foil or the gauge strip depending on the application field. It is thus possible to apply staining or discoloring layers to the external gauging areas to permit the dentist to determine the contact points of touching teeth in addition to dental contact pressure.

Further, it is advantageous to stabilize an aluminum foil having a thickness of approx. 5 microns to 10 microns with an applied plastic layer. This can be done not only on the outside but also on the inside, but the gauging area (bite area) must remain free of the plastic layer. The plastic has the advantage of avoiding unwanted premature contacts on the insides of the gauge strip; further it gives a gauge strip provided with elevations and depressions a desirable reversibility of the gauging areas, thereby permitting more dynamic measurement.

The linear elevations and depressions are preferably disposed at an angle of 45 degrees to the longitudinal direction of the gauge strip. This ensures that the peaks of the elevations intersect at an angle of 90 degrees when the strip is folded. This permits the gauge strip to be produced more economically.

The elevations and depressions of the gauge strip are preferably produced by the embossing method.

The gauge can be provided for example with a self-adhesive layer to be fastened to the housing of the oscillator. It is also possible to provide the gauge strip with a spring clip for fastening it to the housing. It is also possible to execute the housing of the oscillator so that the gauge can be fastened thereto mechanically, for example with an open sleeve or a spring clip as with a ballpoint pen.

There are further numerous possibilities for detachably interconnecting the gauge and the housing. Thus, openings can be provided on or in the housing through which the gauge, formed for example as a gauge strip, is inserted or threaded.

The gauge can also be applied to an electrically insulating material. The material can be e.g. paper, silk or plastic, in particular an elastic plastic. The plastic is preferably so constituted that the gauge can be cleaned by sterilization.

The sensor is formed for example by a metal foil. Possible metals are e.g. noble metals, such as gold or silver, which can also be applied to an insulating supporting material e.g. by vapor deposition.

It has proved especially advantageous to use a gauge strip of an aluminum material which is passivated with an alumina layer on the inside. The thickness of the alumina layer can be optimized by anodizing the aluminum strip. The gauge strip here has a thickness of preferably less than 200 microns, in particular less than 100 microns. Biting on the gauge strip can destroy the electrically insulating layer at the occlusion points. Thus, if the gauge strip has been wound around the inductance coil once, a further winding arises around the inductance coil and detunes the oscillator. This winding influences the inductance in transformer coupling and changes the frequency of the oscillator upon the action of force. The frequency change caused by the detuning can cause both an increase and a decrease in the natural frequency of the oscillator, depending on the electromagnetic conditions in the frequency-fixing oscillating circuit and the choice of operating point.

Instead of or in addition to the thus caused inductive load, the frequency change can also be caused by a capacitive and/or ohmic load. Thus, the winding formed by destruction of the insulating layer has an ohmic resistance which depends among other things on the mechanical contacting at the occlusion points.

Further, with the gauge strip wound around the inductance coil, the two end portions of the gauge strip that are subjected to the pressure to be determined, i.e. that are bitten on, lie against each other with their insides with the electrically insulating or dielectric layer. Thus, the gauge strip at the same time forms a capacitance which leads to a frequency change, depending on how the thickness of the dielectric layer and thus the distance of the electroconductive foil end portions of the strip and the dielectric constant change during biting.

The evaluation circuit of the inventive apparatus can be a phase locked loop (PLL) circuit and/or for example a PC to which the output signals of the oscillator or the PLL circuit are supplied.

The oscillator can be disposed in a housing with a sleeve-shaped portion around which the gauge strip is wound. Preferably, the oscillator is connected wirelessly to the evaluation circuit. For measuring dental contact pressure, it is thus merely necessary to wrap the gauge strip once around the sleeve-shaped, for example pencil-sized housing, whereupon the patient bites on the superposed end portions of the gauge strip wound around the housing of the oscillator. The sensor or the foil or gauge strip can of course also be connected to the oscillator and/or evaluation circuit via a cable.

The inventive gauge strip preferably has a thickness and flexibility corresponding to a conventional occlusion foil with discoloration. It can be provided on its outside additionally with a coating for detecting the occlusion points by staining or discoloration to obtain further measuring data.

The output signals of the evaluation circuit can be for example stored in a memory and/or supplied to a display. The display can be formed for example by a bar of light-emitting diodes.

Since the inventive apparatus works in the low-impedance range, it is not influenced by galvanic effects which can occur e.g. in saliva. This also permits a favorable structure of the electronics for complying with electronic safety regulations.

A preferred embodiment of the gauge strip has an electroconductive layer in the gauging areas. Thus, the transition resistance of the gauging areas is homogenized and the characteristic improved by a steadier measuring signal. Further, e.g. a conductive gel has the advantage of forming adhesion of the gauging area, so that the end portions of the gauge strip are fixed together and handling thus simplified for the dentist.

A preferred embodiment of the gauge strip has a foil laminate having on the inside an insulating layer (preferably a polymer or adhesive layer), then the electroconductive layer, then a stabilizing layer (preferably a polymer), whereby at least the gauging areas are provided with elevations and depressions such that their peaks intersect when the gauge strip is folded during actual measurement.

The gauge strip as a laminate preferably has a thickness of at most 15 microns, so that the gauging area reaches a maximum thickness of 30 microns in the folded state.

Such an inventive gauge strip has the advantage of adapting to the three-dimensional form of the teeth during measurement and involving no blocking effect to hinder the final bite. This permits dental contact pressure measurement or chewing pressure measurement in a natural position of the teeth.

For easier handling the gauge strip or a gauge is preferably already incorporated into a part to be slipped onto the inductor (cap, sleeve) or fastenable thereto with an adhesive layer.

The user in dentistry is enabled by the inventive force transducer, together with the use of a gauge strip having a spacer mounted thereon on at least one gauging area, to determine the preparation height of a tooth to be prepared or to specifically detect that the required preparation height is not met. The production of dental prostheses, such as crowns, bridges, implant superstructure constructions, etc., requires a certain minimum thickness of the prosthesis, depending on the type (all-ceramic, metal ceramic, polymer, etc.). For example, an all-ceramic crown should reach a minimum thickness of 1.5 mm to 2 mm in the area facing the antagonist to be able to withstand the mechanical influences during chewing. If this minimum thickness is not met, there is a danger of the dental prosthesis being destroyed during biting. A dental prosthesis with a metal framework also requires a certain minimum height, which in this case serves primarily an esthetic purpose, since the dental technician, to obtain a natural appearance of the artificial tooth, must apply several veneer layers to the metal framework forming a dark core. On the other hand, the dentist should remove only the absolutely necessary natural tooth substance when preparing the tooth despite the required minimum heights to avoid permanently damaging it. In the usual check of the preparation the dentist can in many cases not recognize exactly whether he has reached the minimum height in really all areas of the prepared tooth due to the uninspectability when the teeth are closed. When applying the invention he places the gauge strip with the spacer on the tooth to be prepared when the teeth are open. Biting compresses the preferably flexible or rubber-elastic material, since the spacer has a thickness or height that is above the required minimum height. The most pressure is exerted on the gauge strip at the places where the greatest compression is present. This permits the measurement or definition of the smallest distance between prepared tooth and antagonist.

The invention will hereinafter be explained in more detail by way of example with reference to the drawing, in which:

FIG. 9 shows a plan view of the inside of an open gauge strip with elevations and depressions;

FIG. 10 shows a longitudinal section through the gauge strip according to FIG. 9;

FIG. 11 shows a plan view of the gauge strip wound around the oscillator according to FIG. 9 and FIG. 10 after it is wound around the oscillator;

FIG. 12 shows a plan view of the inside of an open gauge strip with elevations and depressions according to another embodiment;

FIG. 13 shows a longitudinal section through the gauge strip according to FIG. 12;

FIG. 14 shows a cross-section through the lower area of the gauge strip according to FIG. 12;

Figure 1:
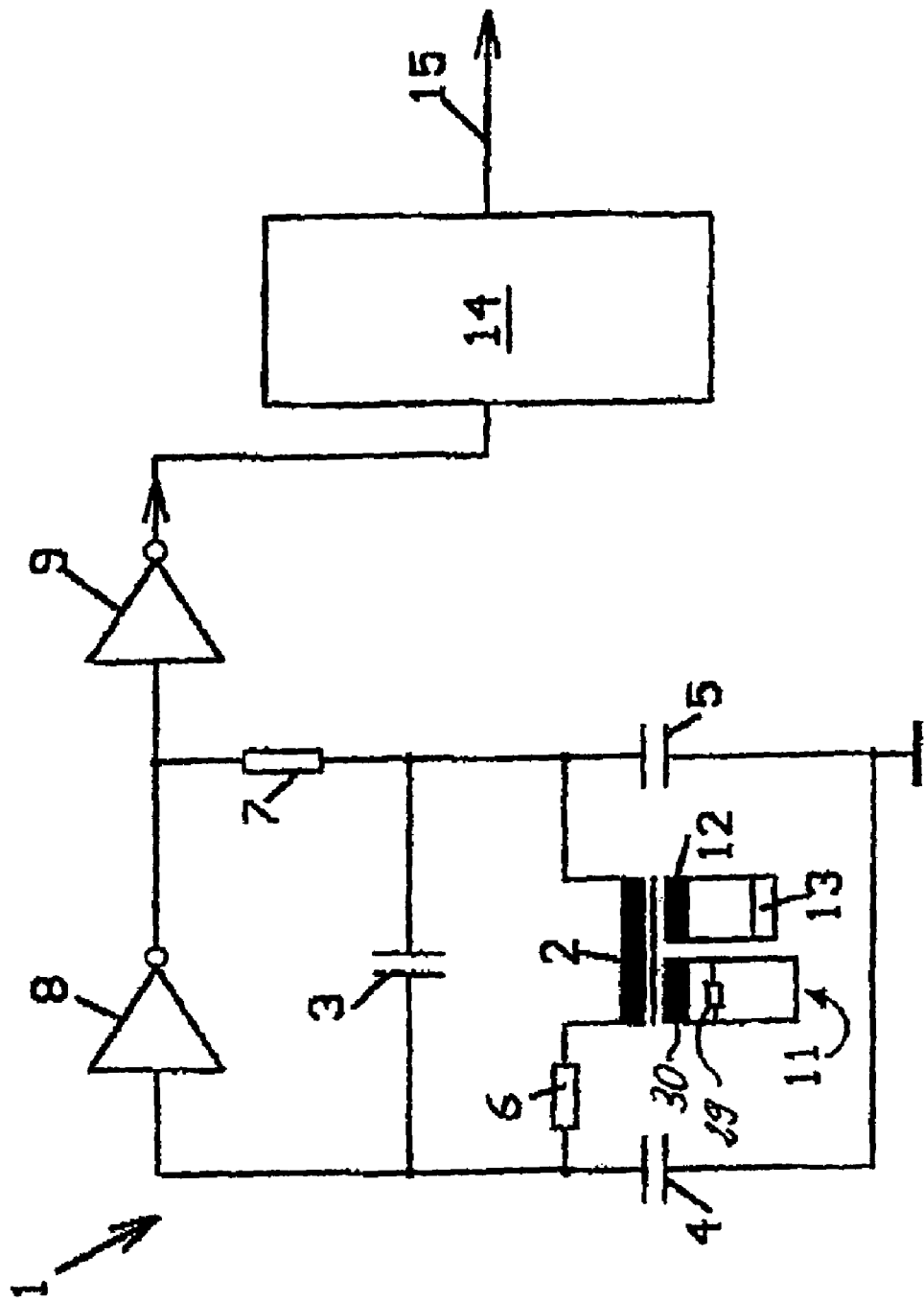
FIG. 1 shows an embodiment of the circuit of the inventive apparatus.

According to FIG. 1 the oscillator 1 has a self-oscillating circuit with an inductor 2 in the form of an inductance coil, a plurality of capacitors 3, 4, 5, two ohmic resistors 6, 7 and two Schmitt trigger inverters 8, 9 for forming the output signals. The two Schmitt trigger inverters 8, 9 are supplied for example with a 5 V extra-low voltage source (e.g. accumulator or battery) not shown.

The sensor or gauge 11 is formed as an integral gauge strip and has at least one winding which forms a secondary winding 30 in transformer coupling with the inductor 2, as shown schematically in FIG. 1. Further, a further secondary winding 12 with an ohmic resistor 13 or another load is disposed in transformer coupling with the inductor 2. With the further secondary winding 12 the characteristic of the frequency change can be optimized upon the action of a force on the gauge 11.

The inductor 2 can also be formed as a differential transformer or differential coil. This execution is advantageous in particular when two or more oscillators are provided, as mentioned above. A differential coil is present when the winding 12 is omitted in FIG. 1. However, the winding 12 is present with the differential transformer and disposed symmetrically to the primary winding 2.

The gauge strip can also be formed by a gauge 11 which is connected to the secondary winding 30 via electrical lines. As shown in FIG. 1, the two lines can be connected via a resistor 29. Such a resistor is advantageous when the gauge 11 has inductive, or capacitive, including piezoelectric or piezoresistive, properties.

Figure 2:
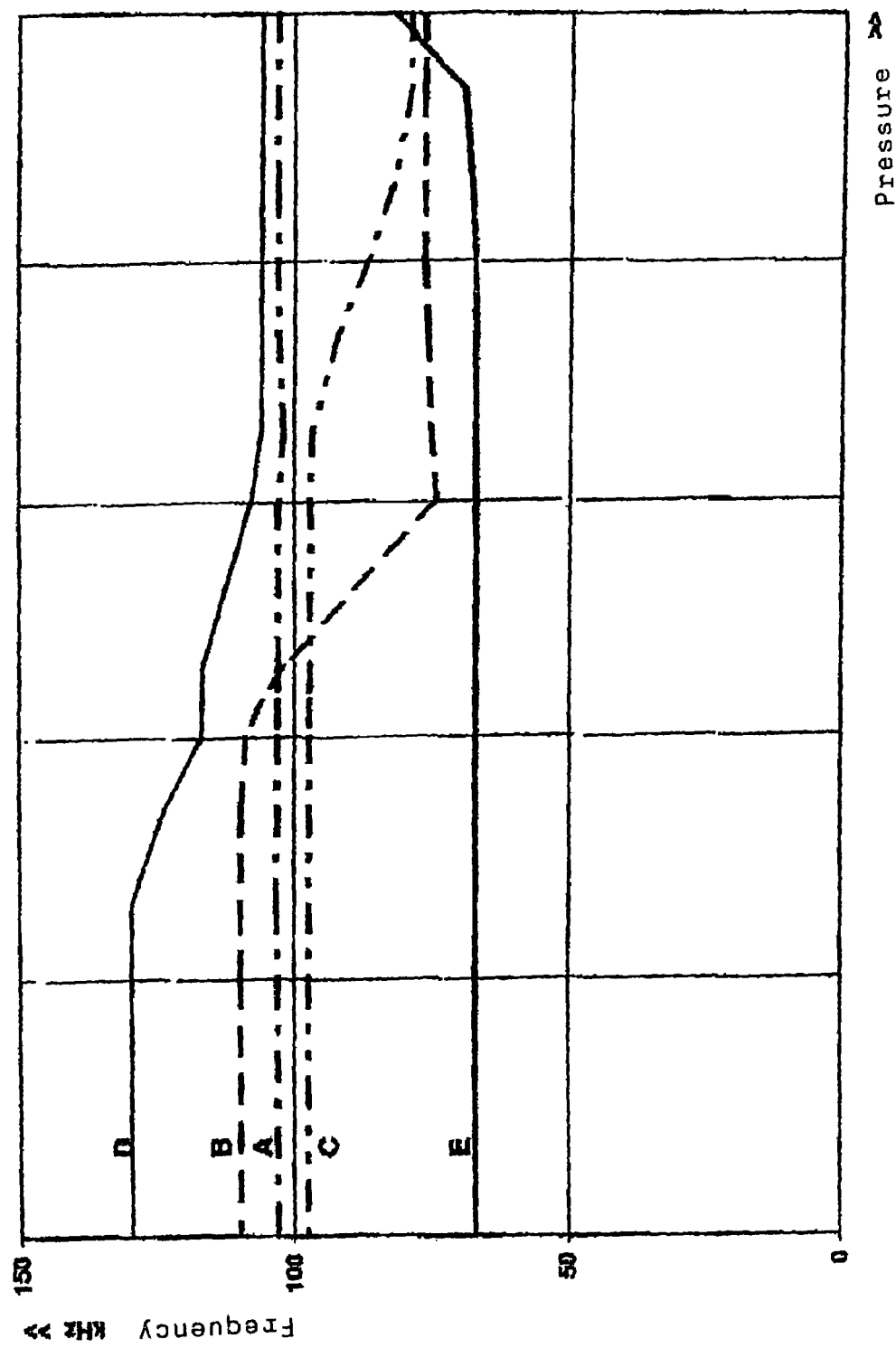
FIG. 2 shows different characteristics of the frequency change with a force acting on the gauge strip/sensor.

FIG. 2 shows five different measuring characteristics A, B, C, D and E, whereby characteristic A is largely useless, while characteristic B has a long proportional range, characteristic C a shorter proportional range and characteristic D two proportional ranges. Characteristic E shows an increase of oscillator frequency upon an increase of measuring force.

The output signals of the inverter 9 are supplied to the evaluation circuit 14 which can be formed for example by a PLL circuit, i.e. a circuit which compares the input frequency with an internal frequency and produces an output signal 15 in case of a frequency difference. While the Schmitt trigger inverter 9 produces a digital output signal for coupling out the signal, the PLL circuit forms an analog output signal. The latter can be changed into a digital signal by an analog-digital converter (not shown) and stored in a memory chip (not shown) and displayed on an LED bar (likewise not shown). Thus, three to ten memory chips can be present, for example, so that three to ten measurements can be displayed in succession on three to ten light bars. This representation allows the dentist to measure bite force and tooth distance several times before, during and after the dental work to be carried out.

Figure 3:
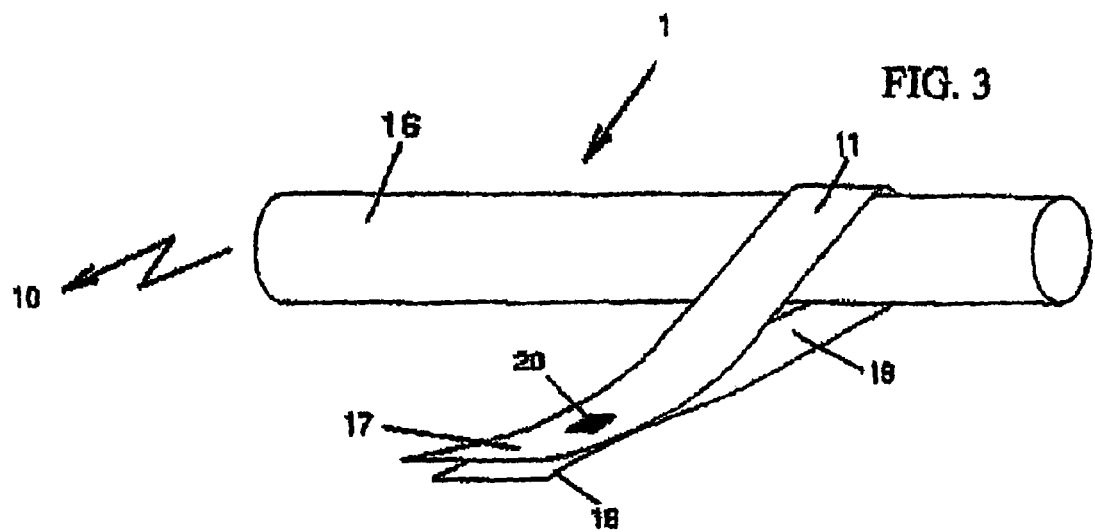
FIG. 3 shows a gauge strip wound around the housing of the oscillator in a perspective view.

According to FIG. 3 the oscillator 1 (FIG. 1) is disposed in a sleeve-shaped, approximately pencil-sized housing 16. The oscillator is connected wirelessly to the evaluation circuit 14 (FIG. 1) as indicated by the arrow 10.

The gauge strip 11 is wound in FIG. 3 once around the housing 16 in the area of the inductance coil 2 (FIG. 1). Its end portions 17, 18 thus form superposed tabs. The gauge strip 11, which has a width corresponding approximately to a tooth, consists for example of an aluminum foil provided on its inside 19 with an insulating alumina layer. For measuring occlusion pressure, the patient bites on the superposed tabs 17, 18. This causes the alumina layer to be destroyed at the occlusion point 20, or at least its layer thickness to be reduced so as to give rise to a closed, electroconductive winding which changes the inductance and thus the frequency of the oscillator 1 (FIG. 1). To increase the measuring effect, the gauge strip 11 can also be wound around the housing several times. The gauge strip can also consist of a metal foil without an insulating layer. The transition resistance between the tabs 17, 18 then depends on the occlusion pressure.

Figure 4:
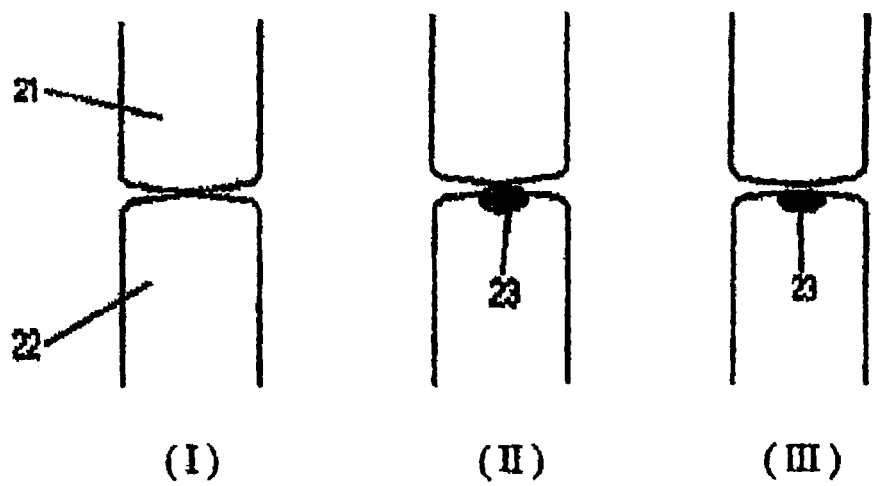
FIG. 4 shows schematically the occlusion pressure before and after a dental filling.

If according to FIG. 4 the patient is for example given a filling in the mandibular tooth 22 occluding with the maxillary tooth 21, occlusion pressure is measured as a reference before filling and stored according to (I). Then the tooth 22 is provided with the filling 23 according to (II), and the filling ground down (III) until the reference occlusion pressure as before filling (I) comes about. When dental prostheses such as crowns, bridges, etc., are inserted it has proved advantageous if the pressure or the distance of the teeth adjacent to the dental prosthesis is determined in a reference measurement before, during and after insertion.

Figure 5:
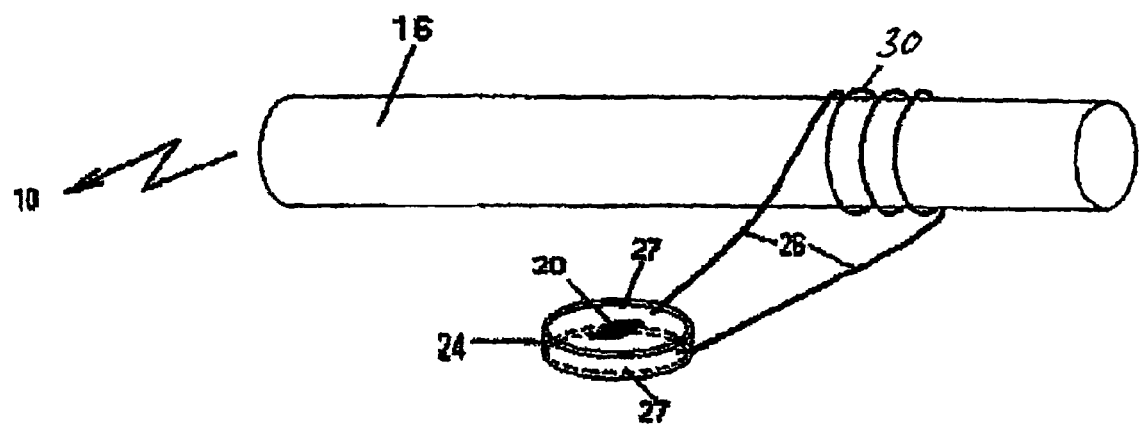
FIG. 5 shows a secondary pickup winding wound around the housing of the oscillator, with a piezoelectric element, in a perspective view.

In FIG. 5, secondary winding 30 is wound several times around the housing 16 in the area of the inductance coil 2 (FIG. 1). The two leads 26 of the secondary winding 30 are connected to the two piezoelectrodes 27 of the piezoelectric element 24. Exertion of pressure on the occlusion point 20 influences the piezoelectric element 24 as described above, thereby detuning the oscillator and thus permitting determination of occlusion pressure.

Figure 6:
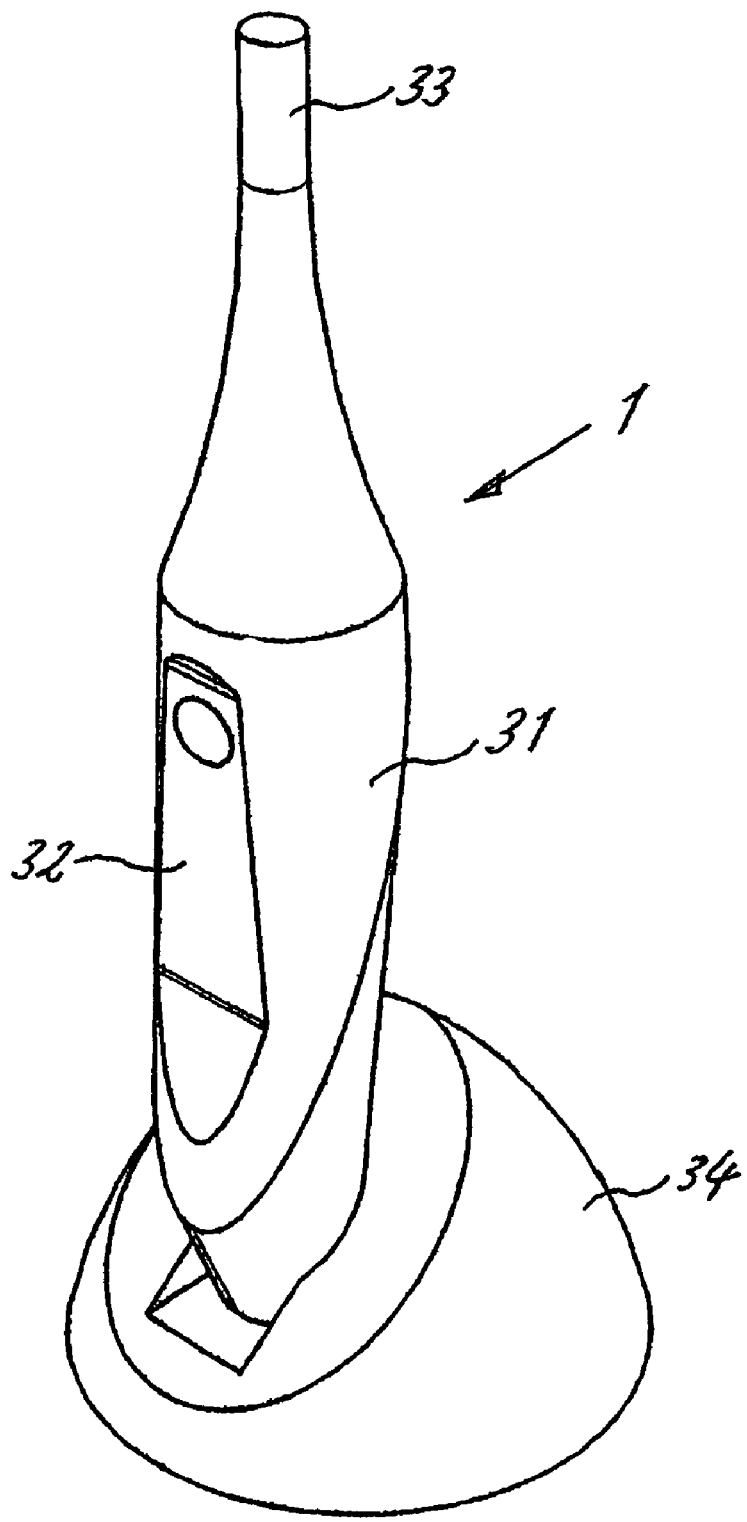
FIG. 6 shows a perspective view of the oscillator for a gauge for determining tooth occlusion, dental contact pressure and/or chewing force.
Figure 7:
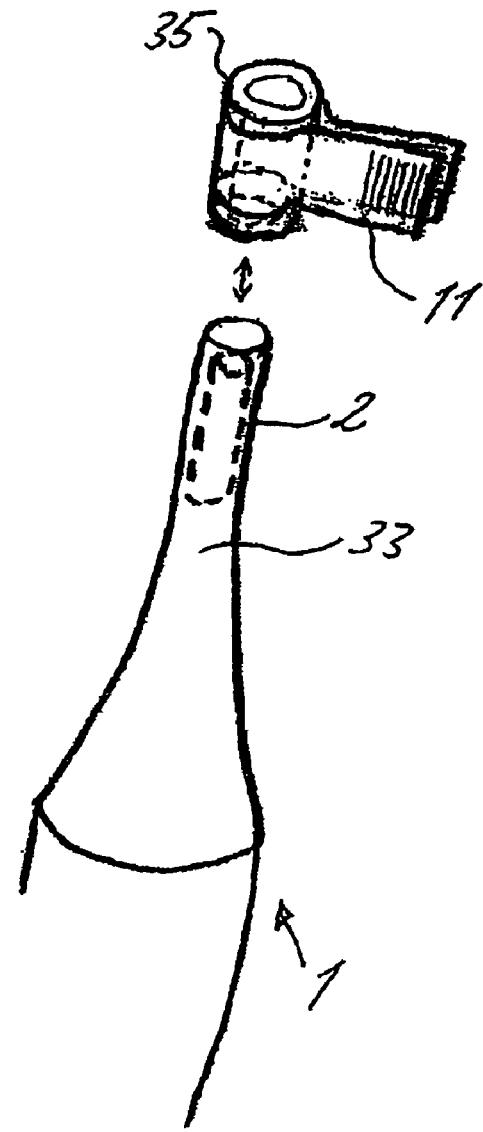
FIG. 7 shows a perspective view of the part of the oscillator according to FIG. 6 with the primary winding and a slip-on element to be slipped onto the force measuring transducer, with a gauge strip applied thereto.

According to FIG. 6 and FIG. 7, the oscillator 1 has a hand grip 31 with a switch 32 for actuating the oscillator, and a tapered portion 33 in which the inductor 2 is disposed, as indicated by the dashed line in FIG. 7. The oscillator 1 is received by a charging station 34 which is coupled inductively with the oscillator 1.

As apparent from FIG. 7, the gauge strip or gauge 11 can be provided on a slip-on element 35 to be slipped e.g. in the form of a sleeve or cap onto the tapered portion 33 with the inductor 2. The gauge 11 can be fastenable e.g. adhesively to the slip-on element 35.

Figure 8:
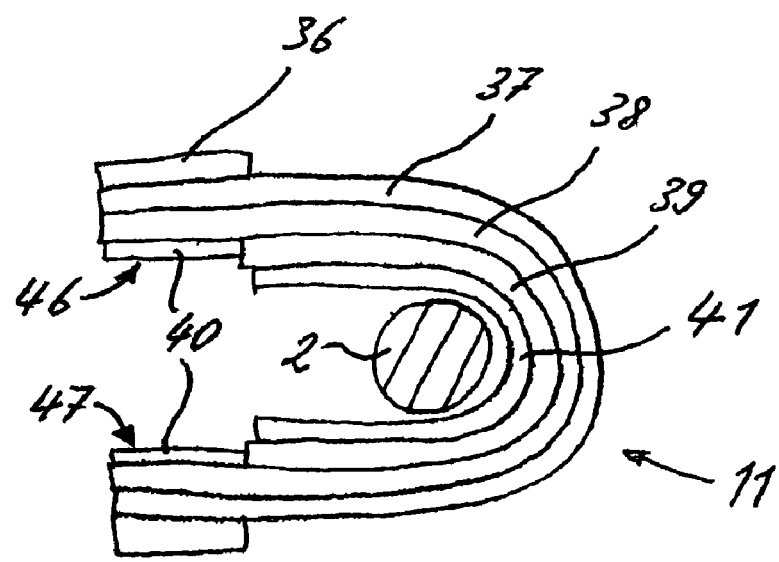
FIG. 8 shows a longitudinal section through a gauge strip according to another embodiment.

In the embodiment according to FIG. 8, the gauge strip 11 wound around the inductor 2 is built up from a plurality of functional layers 36 to 41. The outermost layer 36 provided on the two end portions of the gauge strip 11 is formed by a staining and/or discoloring material for determining the tooth contact points. The adjacent layer 37 is an electrically insulating and stabilizing carrier layer, preferably made of a plastic material, for the adjacent electroconductive layer 38, which consists for example of a metal such as aluminum. On the inside of the layer 38 there is a further electrically insulating layer 39, e.g. made of plastic, but it does not cover the gauging areas at the two ends of the gauge strip 11. The layer on the gauging areas 40 on the inside of the gauge strip is formed by an electroconductive and deformable material, for example a gel. Further, an adhesive layer is applied to the inside of the gauge strip, ending before the two gauging areas 40 and serving to fasten the gauge strip 11 to the slip-on element 35 or directly to the tapered area 33 of the oscillator.

In the embodiment according to FIG. 9 to FIG. 11, the gauge strip 11 has elevations 43 and depressions 44 which extend alternately and linearly parallel beside each other. The linear elevations 43 and depressions 44 are disposed obliquely to the longitudinal axis of the gauge strip 11.

As shown in FIG. 11, the elevations 43 and depressions 44 thus intersect on the superposed gauging areas of the end portions of the gauge strip 11 when it is wound around the oscillator portion 33.

If the gauge strip 11 or gauge consists of electroconductive material, the intersecting peaks 45 of the elevations 43 (FIG.

16) form electrical contact surfaces whose size increases when the gauging areas of the gauge strip 11 are pressed together. The enlargement or reduction of the contact surface causes the electrical transition resistance of the gauge strip 11 to be reduced or enlarged accordingly.

Figure 16:
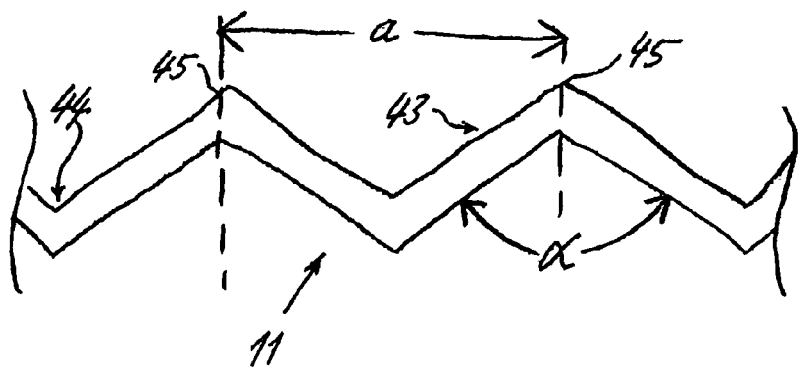
FIG. 16 shows an enlarged view of the cross-section of the gauge strip according to FIG. 9 to FIG. 11.

The angle alpha assumed by the peaks 45 can be e.g. 120 degrees, as shown in FIG. 16. The distance a from one peak 45 to the next peak 45 is preferably smaller than 0.5 mm.

Figure 15:
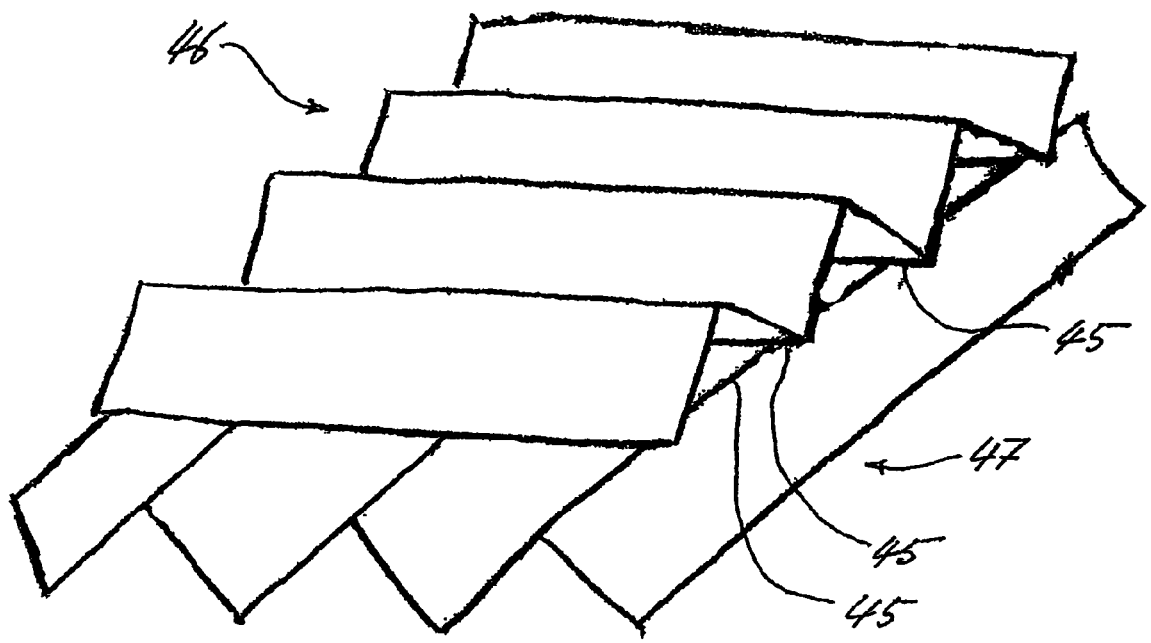
FIG. 15 shows a perspective view of the end portions of the gauge strip after it is wound around the oscillator.

FIG. 12 to FIG. 14 show another embodiment of the gauge strip 11 or gauge which differs from the embodiment according to FIG. 9 to FIG. 11 essentially in that the elevations 43 and depressions 44 are provided only in the gauging areas 46 and 47 on the end portions of the gauge strip 11 and extend in the one area 46 transversely to the gauge strip 11 and in the other area 47 longitudinally thereto. As apparent from FIG. 15, the peaks 45 of the elevations thus intersect at an angle of 90 degrees.

Figure 17:
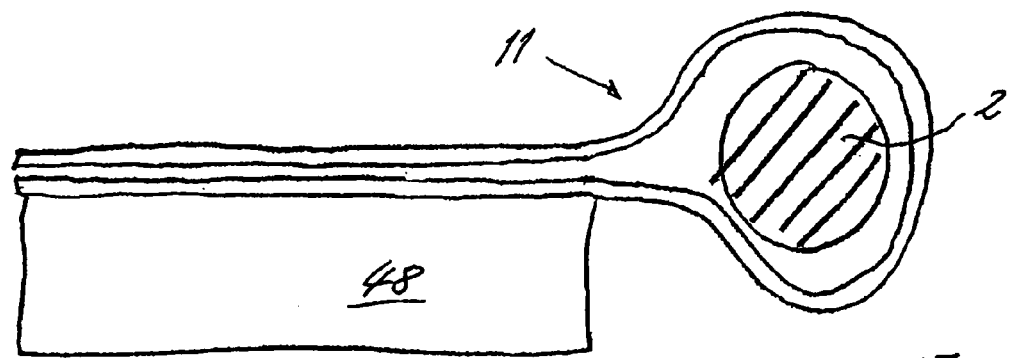
FIG. 17 shows a longitudinal section through a gauge strip wound around an oscillator, with a spacer made of compressible material.

The gauge 11 according to FIG. 17 has at least on one outer side of the gauging area a spacer 48 made of a compressible material formed for example by a rubber-elastic plastic material.

Figure 18:
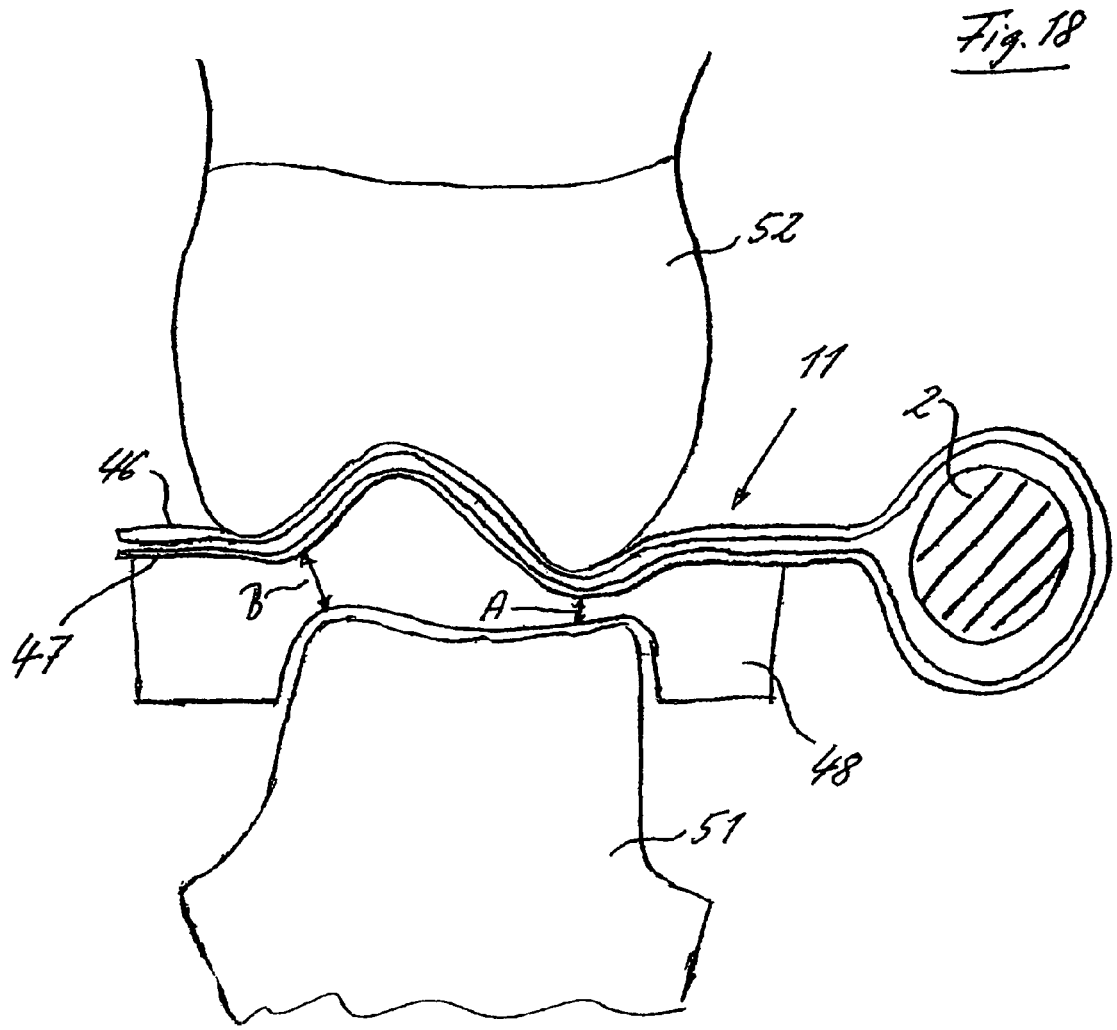
FIG. 18 shows a schematic view of the gauge strip according to FIG. 17 between two opposite teeth in the final bite.

FIG. 18 shows the gauge according to FIG. 17 during the final bite between a prepared tooth 51 and the opposite tooth 52 during the final bite. It can be seen that the gauge 11 adapts to the form of the tooth 52. Further, the prepared tooth 51 compresses the spacer 48. This causes the spacer 48 to be pressed against the gauge 11, with a different pressure depending on the compression. As apparent from FIG. 18, a greater pressure is thus exerted at A by the spacer 48 on the portion of the gauging areas 46, 47 disposed there than at B. The thickness of the spacer 48 can be chosen so that the distance A is determinable. This is possible because the compressible material of the spacer 48 leads as of a certain thickness to a clear increase in pressure on the gauging areas 46, 47 and thus to a frequency change of the oscillator 1. This makes it possible for the user to determine e.g. in area A whether, when preparing a tooth, he has reached the preparation height required for the dental prosthesis to be formed.

What is claimed:

1. A force measuring transducer, comprising at least one oscillator with at least one inductor formed by a primary winding and at least one gauge which is connected electroconductively with a secondary winding, the secondary winding being disposed in transformer coupling with the inductor of the primary winding to generate a change in frequency of the oscillator in response to force applied to the gauge, wherein action of the force on at least one gauging area of the gauge changes the impedance of the gauge and the load of the inductively coupled secondary winding which varies the frequency of the oscillator, and an evaluation circuit connected to the oscillator for receiving the frequency from the oscillator and determining a resulting frequency change of the oscillator which is proportional to the force acting on the gauge.

2. A force measuring transducer according to claim 1, wherein the oscillator has at least one capacitor, at least one resistor, and at least one further inductor.

3. A force measuring transducer according to claim 1, wherein the oscillator is connected wirelessly to the evaluation circuit.

4. A force measuring transducer according to claim 1, wherein the gauge has a thickness of no more than 30 microns in a gauging area.

5. A force measuring transducer according to claim 1, wherein the inductor has associated therewith an additional secondary winding with a load for optimizing a measuring characteristic.

6. A force measuring transducer according to claim 1, wherein the gauge and the secondary winding electrically connected thereto are isolated galvanically from the circuit of the oscillator.

7. A force measuring transducer according to claim 1, wherein the gauge has inductive properties and/or capacitive properties and/or ohmic properties.

8. A force measuring transducer according to claim 7, wherein the gauge has ferroelectric properties or pyroelectric properties or ferromagnetic properties.

9. A force measuring transducer according to claim 7, wherein the gauge has piezoelectric and/or piezoresistive properties.

10. A force measuring transducer according to claim 1, wherein the gauge has ferroelastic or magnetoelastic properties.

11. A force measuring transducer according to claim 1, wherein at least one of an electrically insulating layer and an electroconductive layer is formed as part of said gauge to be destructible by action of pressure.

12. A force measuring transducer according to claim 1, wherein the oscillator is provided in a housing, a portion of said housing with the inductor having the secondary winding disposed thereabout.

13. A force measuring transducer according to claim 1, wherein the gauge and the secondary winding are formed integrally.

14. A force measuring transducer according to claim 1, wherein the gauge comprises an electroconductive gauge formed integrally with the secondary winding and having ferromagnetic properties, the gauge being disposed at least partly within the primary winding of the inductor as an inductive core.

15. A force measuring transducer, comprising at least one oscillator with at least one inductor formed by a primary winding and at least one gauge connected electroconductively with a secondary winding, the secondary winding being disposed in transformer coupling with the inductor of the primary winding to generate a change in frequency of the oscillator in response to force applied to the gauge, at least one gauging area of the gauge comprising a foil, wherein action of the force on the foil of said at least one gauging area changes the impedance of the gauge and the load of the inductively coupled secondary winding which varies the frequency of the oscillator, and an evaluation circuit connected to the oscillator for receiving the frequency from the oscillator and determining a resulting frequency change of the oscillator which is proportional to the force acting on the gauge.

16. A force measuring transducer according to claim 15, wherein the foil comprises at least one of an electroconductive material and a material with magnetoelastic properties.

17. A force measuring transducer according to claim 15, wherein the gauge has on at least one of an inside and an outside thereof at least one functional layer.

18. A force measuring transducer according to claim 17, wherein the functional layer has properties that are at least one of insulating, electroconductive, stabilizing, reversible, adhesive, staining, discoloring, chemically reacting upon action of force, insulating and destructible upon action of force.

19. A force measuring transducer according to claim 17, wherein the inside of the gauge has applied thereto in the gauging area, said further functional layer comprising an electroconductive liquid or electroconductive gel.

20. A force measuring transducer according to claim 15, including a spacer provided on the foil of said at least one gauging area.

21. A force measuring transducer according to claim 20, wherein the spacer comprises elastic material that is compressible upon action of a force.

22. A force measuring transducer according to claim 15, wherein in said at least one gauging area the foil has elevations and depressions which are deformed in dependence on the extent of the action of force exerted on the foil.

23. A force measuring transducer according to claim 22, wherein the elevations and the depressions extend alternately and linearly parallel beside each other.

24. A force measuring transducer according to claim 22, wherein the foil is formed such that peaks of the elevations of one said gauging area intersect peaks of the elevations of a second superposed one of said gauging areas.

25. A force measuring transducer according to claim 24, wherein the peaks of the foil comprise linearly parallel extending peaks of the elevations of two of the gauging areas so that the gauging areas intersect at an angle of from approximately 70 degrees to 110 degrees.

26. A force measuring transducer according to claim 24, wherein the peaks of the elevations enclose an angle ($\alpha$) between 100 degrees and 140 degrees, and the distance from one peak to the next peak is less than 0.5 mm.

27. A force measuring transducer comprising:

at least one oscillator having at least one inductor, at least one capacitor and at least one ohmic resistor, for forming output signals;

a gauge with at least one of piezoelectric and piezoresistive properties connected with at least one winding that forms a secondary winding, the secondary winding being disposed in transformer coupling with the inductor, force on the gauge changing the impedance of the gauge and the load of the inductively coupled secondary winding which changes the inductance of the inductor to vary the frequency of the output signals of the oscillator; and an evaluation circuit for receiving the output signals of the oscillator to determine the change in frequency, wherein the change in frequency corresponds to force applied to the gauge.

28. A force measuring transducer according to claim 27, said gauge including at least one gauging area comprising a foil including a functional layer having properties that are at least one of stabilizing, reversible, adhesive, staining, discoloring, and destructible upon action of force.

29. A force measuring transducer according to claim 27, wherein the force measuring transducer having the gauge with at least one of piezoelectric and piezoresistive properties is free from an amplifier.

\* \* \* \* \*